United States Patent [19]

Simons

[11] Patent Number: 5,153,117
[45] Date of Patent: Oct. 6, 1992

[54] FETAL CELL RECOVERY METHOD

[75] Inventor: Malcolm J. Simons, Fryerstown, New Zealand

[73] Assignee: GeneType A.G., Zug, Switzerland

[21] Appl. No.: 499,932

[22] Filed: Mar. 27, 1990

[51] Int. Cl.$^5$ .............................. C12N 1/00; C12Q 1/24
[52] U.S. Cl. ............................................ 435/2; 435/6;
435/7.21; 435/7.24; 435/29; 435/30;
435/240.21; 435/243; 436/503; 436/800;
436/824
[58] Field of Search ...................... 435/2, 6, 7.21, 7.24,
435/29, 30, 240.21, 243; 436/503, 800, 824

[56] References Cited

U.S. PATENT DOCUMENTS

| | | | |
|---|---|---|---|
| 4,675,286 | 6/1987 | Calenoff | 435/7 |
| 4,835,098 | 5/1989 | Orr et al. | 435/6 |
| 4,987,086 | 1/1991 | Brosnan et al. | 436/501 |

FOREIGN PATENT DOCUMENTS 9006509  6/1990  PCT Int'l Appl.

OTHER PUBLICATIONS

I. M. Roitt, *Essential Immunology*, 5th Edition, Blackwell Scientific Publications, Oxford UK, 1984, pp. 278-279.

L. A. Herzenberg et al, *Proc. Natl. Acad. SCI U.S.A.*, 76, 1453-1455, 1979.
Iverson et al, *Prenatal Diagnosis*, 61:61-73 (1981).
Bianchi, et al, *Cytometry*, 8:197-202 (1987).

*Primary Examiner*—David Saunders
*Attorney, Agent, or Firm*—Skjerven, Morrill, MacPherson, Franklin & Friel

[57] ABSTRACT

The present invention provides a method for selectively recovering fetal cells from a maternal blood sample. The method comprises the following steps. Cells of the sample are combined with a first and a second antibody labeled with different fluorochromes for a period of time sufficient for antibody binding to produce labeled cells. The antibodies are specific for two different antigens expressed by two material HLA alleles. In a preferred embodiment, the alleles are of an HLA locus for which the woman is heterozygous. Cells having two different fluorescent labels are separated from cells having either a single fluorescent label or unlabeled cells using fluorescence-activated cell sorting. The separated single-labeled and unlabeled cells are recovered. The separated fetal cells can be used in a variety of procedures including DNA amplification methods and karyotyping.

17 Claims, No Drawings

FETAL CELL RECOVERY METHOD

FIELD OF THE INVENTION

The present invention relates to a method for recovery of fetal cells from maternal blood using fluorescence-activated cell sorting.

BACKGROUND OF THE INVENTION

The examination of fetal cells for early detection of fetal diseases and genetic abnormalities is undertaken in approximately one out of every thirty pregnant women. The main indication is maternal age (over 35 years). The tests may involve DNA gene typing or, more commonly, the use of live fetal cells for chromosomal karyotyping.

Fetal cells are usually obtained by amniocentesis, the removal of amniotic fluid from the amniotic cavity within the amniotic sac or placenta. The procedure presents a risk of harm to the fetus, particularly after the first trimester of pregnancy. The risk to the fetus together with the high cost of the procedure have prevented the establishment of examination of fetal cells for early detection of abnormalities as a routine procedure in pregnancy.

In the late 1970s and early 1980s, Herzenberg and his colleagues reported that fetal cells were present in maternal blood as early as 15 weeks gestation. The authors separated maternal and fetal cells using fluorescence-activated cell sorting (FACS) by staining maternal blood for a distinguishing paternal HLA antigen. The authors state that the demonstration that fetal cells enter maternal circulation and can be isolated by FACS-enrichment procedures could have practical significance in enabling karyotyping without the need for amniocentesis. The authors state that this would be possible if the frequency of successful isolation of cells at 15 weeks is sufficiently high and the cells could be induced to divide (enter metaphase). Furthermore, extensive HLA typing reagents, or other cell surface reagents would need to be developed to distinguish maternal and fetal cells. To date, the technique has not been successfully adapted for use as a clinical technique for either karyotyping or fetal DNA analysis.

Recently, fetal cells present in maternal blood have been used to perform analysis of genes present in the fetus. In one technique, the maternal and fetal cells were not separated and the DNA from the cell mixture is amplified with Y chromosome-specific primers to determine whether the fetus is male. It has been suggested that DNA amplification techniques can also be performed to detect gene sequences associated with disease in this manner. Of course, the method cannot be used where the mother is a carrier for the trait.

To date, amniotic fluid has been the only source of antenatal cells to provide a sufficient number of live cells for karyotyping. Furthermore, DNA analysis methods have only been possible in relatively limited situations which depend on particular differences in maternal and fetal cells, e.g. presence of the Y chromosome in the fetus or presence of HLA-A2 antigen on fetal, but not maternal, cells.

DESCRIPTION OF THE PRIOR ART

Herzenberg and his colleagues have described methods for separating maternal and fetal cells in maternal blood using fluorescence-activated cell sorting (FACS). In Herzenberg et al, *Proc. Natl. Acad. Sci. USA* 76:1453–1455 (1979), cells in blood samples from 15-week pregnant HLA A2-negative women were stained for HLA A2 antigen. Stained cells were separated by FACS and collected to enrich the population of fetal cells. Although the technique was demonstrated to effectively identify male, HLA A2-positive cells in maternal blood, to date the technique has not been successfully adapted for general applicability. In Iverson et al, *Prenat. Diag.* 1:61–73 (1981), peripheral blood lymphocytes (PBLs) from either 15 week or 21 to 25 week pregnant women were examined. If the woman was HLA A2-negative, her cells were stained with anti-HLA A2 reagents, sorted by FACS onto microscope slides (for fetuses who were HLA A2-positive), stained with quinacrine and examined microscopically for Y chromatin-positive cells. The authors report that fetal cells enter the maternal circulation as early as 15 weeks gestation.

Bianchi et al, *Cytometry* 8:197–202 (1987) report a technique that allows direct hybridization to the DNA of cells which were flow sorted onto nitrocellulose filters which eliminates the need for a DNA isolation step. The method was performed on human cord blood. The authors state that the technique is useful in situations where there is a limited amount of DNA available for analysis such as for fetal cells recovered from maternal blood.

U.S. Pat. No. 4,675,286 (to Calenoff, issued Jun. 23, 1987) describes a method for obtaining fetal cells for diagnostic examination in which detached cells from the uterine cavity and outer surface of the amniotic sac are incubated with a separation antibody which binds preferentially to either fetal or maternal cells. The antibody can be bound to an insoluble support or conjugated with a fluorescent label and removed with a cell sorter to effect separation.

Truneh et al, *Cytometry* 8:562–567 (1987) describe a method for detection of very low receptor numbers on cells by flow cytometry. The method involves staining the cells with vesicles containing thousands of fluorochrome molecules, which vesicles are conjugated to antibodies with the desired specificity.

Albright et al, *Cytometry* 7:536–543 (1986) describe the use of centrifugal separation of cells in sputum specimens as an alternative to flow cytometry.

*Society for Clinical Cytology* 1988 *Abstracts* p.6 describe in situ hybridization for detection of structural and numerical abnormalities using nonradioactive probes for detection of aneuploidy and translocations (Pinkel et al, No. 13). The immunopotentiality of cancer patients was studied by sorting peripheral blood T cell subsets by a multiparameter analysis using monoclonal antibodies and flow cytometry (Nonura et al, No. 14).

*Practical Flow Cytometry* (Second Edition) by Howard M. Shapiro, Alan R. Liss, Inc. 1988 is a comprehensive work on flow cytometry. The book describes how to build, purchase and use a flow cytometer and how to design analyses and analyze the data produced thereby.

Each of the above-described references and the references cited therein is incorporated herein by reference in its entirety.

SUMMARY OF THE INVENTION

The present invention provides a method for selectively recovering fetal cells from a maternal blood sample. The method comprises the following steps. Cells of the sample are combined with a first and a second antibody labeled with different fluorochromes for a period of time sufficient for antibody binding to produce labeled cells. The antibodies are specific for two different antigens expressed by two HLA alleles. In a preferred embodiment, the alleles are of an HLA locus for which the woman is heterozygous. Cells having two different fluorescent labels are separated from cells having either a single fluorescent label or unlabeled cells using fluorescence-activated cell sorting. The separated single-labeled or unlabeled cells are recovered.

The method is based on using antibodies specific for two maternal HLA antigens to label the cells of a maternal blood sample. The maternal cells are double-labeled. Except when the fetus inherits both maternal alleles, fetal cells are either single-labeled or unlabeled. In a preferred embodiment, the alleles are for a single HLA locus. In this way, the maternal cells are double-labeled, and the fetal cells, having inherited only one of the two maternal alleles, are single-labeled. In instances where the fetus is the same HLA type as the mother for those alleles, no single-labeled or unlabeled cells will be observed. Antibodies specific for another HLA allele can be used until a sample having single-labeled or unlabeled cells is produced.

The separated fetal cells can be used in a variety of procedures. The DNA in the recovered fetal cells can be used to determine a variety of genetic traits, particularly using DNA amplification methods. In a preferred embodiment, the fetal cells are cultured and the cultures used for karyotyping. It is also envisaged that cytogenetic abnormalities classically revealed by karyotyping may also be revealed by gel electrophoresis.

DETAILED DESCRIPTION OF THE INVENTION

The present invention provides a method for selectively recovering fetal cells in a maternal blood sample. The method is based on differentially staining maternal and fetal cells based on differences in the HLA surface antigens of the cells. A fetus inherits one allele for each HLA locus from the mother. When two selected maternal alleles are for different loci, there is a one in four chance that the fetus will inherit both alleles. Three out of four times, the fetus will inherit either one or neither of the two maternal alleles. When the mother is heterozygous for an HLA locus and the fetus does not inherit the nontransmitted maternal allele from the father, the mother and fetus have different alleles for the HLA locus. Therefore, when a maternal blood sample is combined with antibodies labeled with different fluorochromes for each allele of an HLA locus, the blood sample contains double-labeled maternal cells and single-labeled fetal cells. Single-labeled and unlabeled cells are separated from double-labeled cells using fluorescence-activated cell sorting (FACS), resulting in separation and recovery of fetal cells.

The recovered fetal cells can be used in a variety of assays. The DNA in the recovered fetal cells can be used to determine a variety of genetic traits. In a preferred embodiment, the fetal cells are cultured and the cultures used for karyotyping. It is also envisaged that cytogenetic abnormalities classically revealed by karyotyping may also be revealed by gel electrophoresis.

The present fetal cell recovery method provides advantages which could not be achieved in prior art methods. Specifically, the method does not rely on attempting to label with discriminating paternal alleles that the child may have inherited. No information regarding the paternal contribution is necessary. Only maternal HLA alleles need to be identified. Not only is there no need to identify alleles of the natural father that may be distinguishing, but, so long as the fetus does not inherit nontransmitted maternal alleles from the father, only a limited number of antigens need be investigated to find a staining pattern that distinguishes maternal and fetal cells. Furthermore, the presence of either single-labeled or unlabeled cells in the sample indicates that the fetal cells are differentially stained. No additional evaluation needs to be made.

The method also does not attempt to distinguish the fetal cells based on "fetal" antigens such as fetal hemoglobin which may also be expressed by some maternal cells. In the present method, once a staining combination is found that results in single-labeled or unlabeled cells being detected in the sample, all of those single-labeled or unlabeled cells are fetal cells. Furthermore, all nucleated fetal cells that express HLA antigens are single-labeled or unlabeled because the HLA antigens are characteristic of that fetus, not of a fetal stage of development or of a fetal cell type. Therefore all single-labeled (or unlabeled) cells are fetal cells.

Selection of HLA Antigen for Staining

The fetus inherits half of its HLA alleles from its mother and half from its father. Therefore, the mother and fetus always have at least one allele for each HLA locus in common. The maternal alleles that the fetus does not inherit are unique to the maternal cells except when the fetus inherits the allele from the father. When the maternal cells express two different antigens for one HLA locus that can be detected by antibodies, the antibodies can be labeled with different fluorochromes and used to separate the maternal and fetal cells by FACS.

Methods for determining the HLA type of an individual are well known. For the present method, if the maternal HLA type is known, any HLA antigen-specific antibodies that are available for any two maternal HLA antigens can be used. Preferably the antibodies are specific for the antigens of any HLA locus at which the mother is heterozygous.

When the maternal HLA type is unknown, the alleles for at least one HLA locus, preferably two or more loci, are determined, preferably by using antibodies specific for antigens of that locus. When antibodies specific for two alleles of the locus react with the maternal cells, those antibodies can be used to label fetal cells. In this way, it is clear at the outset of the staining procedure that antibodies which can be used to label the maternal cells are available. Preferably, the loci are any two of the Class I loci (A, B, and C) and the Class II (DR, DQ and DP) loci. Since those loci are commonly typed by serological methods, HLA antigen-specific antibodies for many alleles of those loci are commercially available.

In selecting the HLA alleles to use, the first consideration is the availability of antibodies for the antigens expressed by the alleles. When antibodies for the antigens of a number of alleles present in the mother are available, preferably, the alleles chosen are those that are furthest apart in the DNA sequence to minimize the likelihood of linkage.

Antibodies specific for the antigen of any of the alleles of maternal HLA loci can be selected for use in labeling cells of the maternal blood sample. The antibodies can be polyclonal or monoclonal, preferably monoclonal. Preferably, the antibodies are specific for the two antigens expressed by the alleles of one HLA locus. In another preferred embodiment, the antibodies are specific for both antigens expressed by the alleles of more than one HTA locus. When the fetus inherits the nontransmitted maternal allele(s) from the father, the labeling process is repeated using antibodies to antigens produced by the alleles of another HLA locus or loci.

For those flow cytometers that can perform a four-color sort, the cells can be labeled with antibodies for antigens expressed by four alleles. In that case, preferably, the antibodies are specific for both antigens expressed by the alleles of two maternal HLA loci. Maternal cells are labeled with all four fluorochromes. Fetal cells are labeled with two of the four fluorochromes when none of the nontransmitted maternal alleles is inherited from the father. By using four fluorochromes from two loci, the fetal cells remain distinguishable from the maternal cells even when the fetus inherits one of the nontransmitted maternal alleles from the father. A second staining is only necessary when the fetus inherits both nontransmitted maternal alleles from the father. When the antibodies are for antigens expressed by three or four maternal loci, using the additional dyes increases the likelihood that the fetus did not inherit each of the maternal alleles.

Fetal cells are only indistinguishable from maternal by the method of the present invention in the case where the fetus inherits all six nontransmitted maternal alleles from the father.

Source and Preparation of Cells

The present method is designed to recover fetal cells present in a maternal blood sample, particularly a venous blood sample. Preferably, the pregnant woman is in her first trimester of pregnancy. The sample can be any blood sample which is prevented from clotting such as a sample containing heparin or, preferably, ACD solution. The sample is preferably stored at 0 to 4° C. until use to minimize the number of dead cells, cell debris and cell clumps. The number of fetal cells in the sample varies depending on factors including the age of the fetus, number of fetal/maternal bleeds, the volume of blood in each episode, and the amount of time since the last bleed. Typically, from 7 to 20 ml of maternal blood provides sufficient fetal cells upon separation from maternal cells. Preferably, 30 ml or more blood is drawn to ensure sufficient cells without the need to draw an additional sample. When a second staining is necessary, cells can be incubated at 37.C. for about 2 hours, then washed to remove previously used antibodies. Additional blood samples are not required.

Maternal blood contains three types of nucleated fetal cells: nucleated erythrocytes, syncytiotrophoblasts and lymphocytes. Blood samples are purified to eliminate red blood cells (RBCs). Preferably, the three types of nucleated fetal cells are maintained in the purified sample. RBCs can be eliminated by incubating the cells in a hypotonic solution, e.g., 0.87% ammonium chloride with 0.037% EDTA. Alternatively, peripheral blood lymphocytes (PBLs) harvested by density gradient separation can be used. Although such separations eliminate nucleated erythrocytes and syncytiotrophoblasts from the sample, the majority of the nucleated fetal cells are obtained by such methods.

To purify PBLs, conveniently, a density gradient medium having a density intermediate between the densities of red blood cells (RBCs) and PBLs such as Ficoll-Hypaque and Percoll (both from Pharmacia, Piscataway, N.J.) is used to harvest the PBLs. The layer of PBLs is removed and resuspended in a suspension medium. The cells are washed and the pellet is resuspended in the suspension medium at an appropriate concentration for sorting. The concentration should not be too dilute. However, the flow cytometer can be adjusted to provide an appropriate cell flow rate using relatively concentrated or relatively diluted samples. Preferably the cell concentration is from about $10^6$ to about $5 \times 10^8$, more preferably from about $5 \times 10^6$ to about $1 \times 10^7$ cells/ml.

The suspension medium is a physiologic solution, such as a physiologic buffer, to maintain cell integrity. Most physiologic buffers, e.g. Tris buffer, phosphate buffer (PB), citrate buffer, phosphate buffered saline (PBS) are suitable. Balanced salt solutions such as Earle's balanced salt solution (EBSS), Hank's balanced salt solution (HBSS), and Gey's balanced salt solution (GBSS) are also suitable. Preferably, the suspension medium is a tissue culture medium (e.g., basal medium Eagle and Dulbecco's modified Eagle's medium), more preferably an enriched tissue culture medium suitable for use with lymphocyte cultures such as RPMI 1640. The use of a tissue culture medium, particularly a medium adapted for the growth of the sample cell type, provides an environment which maximizes cell stability.

The suspension medium can additionally be supplemented with a protein source at a relatively high concentration. The protein source can be albumin such as bovine serum albumin (BSA) or, preferably, human serum albumin (HSA) at a concentration in the range of from about 5 to about 10%. Alternatively, the protein source can be serum such as fetal calf serum or human serum at a concentration of from about 5 to about 10%. Since lymphocytes can be stimulated by the presence of foreign antigens, preferably the protein source is human. Most preferred is the use of about 5% autologous plasma which can be harvested from the purified blood sample and is nonimmunogenic.

Alternatively, the protein source can be added to the flow cytometer collection vessel, rather than to the suspension medium, to cushion the fall of the cell into the vessel, enhancing cell stability.

Labeling the Cells

The cells of the blood sample, preferably purified cells, are labeled with fluorescent antibodies specific for the HLA antigens of at least one maternal HLA locus, selected as described previously. The antibodies can be polyclonal or monoclonal, preferably monoclonal. Preparation of polyclonal and monoclonal antibodies for an antigen of interest is well known.

As stated previously, HLA antigen-specific antibodies are commercially available. Typically the HLA Class I loci (A, B and C) and the Class II DR and DQ loci are determined by serological methods. Therefore, antibodies specific for those antigens are readily available. Sources of HLA antigen-specific antibodies include Genetic Systems (Seattle, Wash.) and C6 Diagnostics (Mequon, Wis.).

The antibody is labeled with a dye that facilitates cell sorting, particularly a fluorochrome. Suitable dyes for FACS analysis and/or separation are well known. Those dyes are described in *Practical Flow Cytometry(-Second Edition)* by Howard M. Shapiro, supra, at pages 115-198. Preferred dyes are fluorochromes including fluorescein (e.g., fluorescein isothiocyanate - FITC), rhodamine (e.g., tetramethylrhodamine isothiocyanate -TRITC), phycoerythrin (PE), allophycocyanin (APC) and Texas Red (Molecular Probes, Eugene OR). The combinations of fluorochromes used for labeling are chosen so that distinguishable wavelengths of light are emitted. A preferred combination is a fluorochrome that emits green light together with one that emits red or orange light, e.g., FITC with PE or Texas red.

The antibody can be labeled with the fluorochrome, directly or indirectly, by well known methods. The conjugation methods for attaching labels to antibodies generally can be used for these purposes. Direct labeling methods for dyes such as FITC are described in Catty et al, in "Antisera in Immunoassays with Special Reference to Monoclonal Antibodies to Human Immunoglobulins", IMMUNOASSAYS FOR THE 80's, supra, pp 133-153 and THE HANDBOOK OF EXPERIMENTAL IMMUNOLOGY 4th Edition, Vol. 1: Immunocytochemistry, ed. D. M. Weir, Blackwell Scientific Publications and in the publications cited in those references. The entire contents of each of those references is hereby incorporated by reference.

Preferably the labeled antibody is purified to remove unbound label prior to use. Preferably, the procedure used also purifies the antibody composition to provide the immunoglobulin fraction, more preferably, to provide the IgG fraction for polyclonal antibodies or, for monoclonal antibodies, the IgG or IgM fraction depending on the isotype of the antibody. Procedures for isolating the antibody fraction of an antibody include the use of recombinant protein G for IgG and immunoprecipitation for IgM. Procedures that additionally separate unbound fluorochrome are well known and include use of a DEAE G 35 sephadex (Pharmacia) Ora pp-106 Pharmacia) column. Exemplary purification procedures are described in detail in the examples.

For dyes such as PE which are more difficult to attach while maintaining antibody activity, the antibody can be labeled with biotin. The dye can be attached by incubation of the biotinylated antibody with PE-avidin or PE-strepavidin (which are commercially available) either concurrently with or, preferably, following incubation of the antibody with the cells. A procedure for conjugating biotin to an antibody is described in Edward A. Bayer et al, "The Avidin-Biotin Complex in Affinity Cytochemistry", in METHODS IN ENZYMOLOGY Vol. 62 (1979) That article is incorporated herein by reference in its entirety.

An exemplary preferred direct labeling method for FITC is described in detail in the examples. A preferred indirect labeling method for biotinylation of an antibody and attachment of PE-strepavidin is also described.

To label the cells with the labeled, HLA antigen-specific antibodies, the cells are incubated with the antibodies for a time sufficient for substantially complete antibody binding under the conditions used. An excess amount of antibody is preferably used. An amount of about 2 $\mu$g for $10^6$ cells is desirable. However, use of 50 $\mu$l of purified antibody at a concentration of about 40 $\mu$g/$\mu$l was sufficient.

The cells are preferably incubated at about 4° C. to maintain cell integrity. Incubation for about 30 minutes at 4° C. is usually sufficient for substantially complete antibody binding. The sample is preferably mixed, as by using a hematology blood rocking device, during the incubation to ensure contact of the antibodies with the cells. Preferably, the incubation is performed in the dark when using a fluorochrome label. Secondary reactions (e.g. incubation of fluorochrome-labeled avidin with biotin-labeled cells) are performed in the same manner.

Exemplary preferred cell labeling procedures for direct and indirect labels are described in detail in the examples.

Sorting Labeled Cells

Flow cytometry is a process in which the measurement of physical and/or chemical characteristics is made while the cells or particles pass, usually individually, through a measuring apparatus in a fluid stream. Biological particles, usually cells, have been subjected to flow cytometric analysis using acoustic, nuclear radiation, electronic and optical sensors. Optical measurements are used for the widest range of applications.

Most of the present applications of flow cytometers derive from the ability of the apparatus to define and quantify heterogeneous cell populations. Physical and chemical characteristics or parameters of cells which can be measured by flow cytometry include cell size, cell shape, pigment content, protein content, DNA content and DNA base ratio. In addition, cells can be labeled with one or more fluorochrome(s) and characterized based on color differences.

The most demanding applications of flow cytometry require identification and subsequent characterization of subpopulations of cells. Both flow sorting and multiparameter analysis are used for this purpose.

Flow sorting employs electrical and/or mechanical means to divert cells with preselected characteristics from the main stream, and can be used to isolate pure populations of viable cells with more homogeneous characteristics than could be obtained by any other means. Flow sorting is particularly useful in circumstances in which further characterization of the selected cells requires short- or long-term maintenance in culture or analytical procedures which cannot be accomplished by flow cytometry.

The parameters which can be used to sort cells include measurements of light scattered by cells at two different angles (less than 2°, commonly called forward scatter, and about 90°) from an incident laser beam. The fluorescence measurement capability of a multiparameter flow cytometer incorporating the light scattering measurements can then be used to determine other characteristics of the individual cell subpopulations.

For samples containing substantially larger numbers of fetal cells, the cells can be selected by a one or two step separation procedure by binding the cells to solid phase-affixed anti-maternal HLA antigen antibodies. For example, maternal cells and fetal cells bind to a column or other solid phase (such as a tissue culture dish surface or magnetic beads) with the shared maternal antigen antibody. Only maternal cells bind to a column (or other solid phase) having antibody to the antigen the fetus did not inherit. In this way, the fetal cells are separated from the maternal cells when incubated with the antibody to the antigen the fetus did not inherit.

For purposes of the present method, the cells are sorted using the four color patterns produced by differential staining with two fluorochromes as a selection criteria. When using red and green fluorochromes, the four patterns are (1) unstained; (2) red only, (3) green only and (4) red and green.

Following staining or labeling of the cells with a red and a green fluorochrome for each of the two maternal alleles, maternal cells are red and green. Fetal cells are either red or green, depending on the allele the fetus inherited. By selecting cells exhibiting either red or green fluorescence, but not both, the fetal cells can be isolated.

Since most flow cytometers can sort on three parameters, an additional selection criteria can be cell size. This criteria eliminates dead cells, debris and cell clumps. However, when the sample is carefully manipulated and kept refrigerated, dead cells do not appear to be a problem.

In a preferred embodiment, an additional selection criteria is DNA content. Fetal cells having greater than 2C DNA content can be determined using a number of vital-staining fluorochromes such as the Hoechst dyes, DAPI (4'-6-diamidino-2-phenylindole), hydroethidine and 7-aminoactinomycin D (7AMD). The fluorochrome used depends on the labels used to select the fetal cells. A second laser capable of emitting UV light is required to excite Hoechst and DAPI dyes. Each of the above-described dyes can be used with FITC and PE.

A flow cytometer can process about $10^7$ to $10^8$ cells per hour, usually about $4 \times 10^7$ cells per hour. Typically, the sample prepared from about 20 ml of maternal blood includes at least about $2 \times 10^8$ cells which can be sorted in about 5 hours to provide sufficient fetal cells for analysis. However, substantially fewer cells may be required, depending on the analysis method to be used.

The ability of the cell sorter to separate maternal and fetal cells ultimately depends on the percentage of fetal cells in the sample. To obtain a fetal cell sample that is at least about 60% pure (60% of the sorted cells are fetal cells), the fetal cells must constitute about 0.001% of the maternal cells or greater. Preferably, the sample contains 80%, more preferably 90% fetal cells post-sorting.

When 100% purity is desired, the sorted cells can be micromanipulated. For example, cell suspensions containing an individual cell per a preselected volume of suspension medium can be prepared by limiting dilution. Drops containing individual cells can placed in suitable containers (e.g. 96 well plates) and examined visually with a fluorescent microscope to identify single-labeled (or unlabeled) cells. Wells containing those cells can be marked and the cells pooled.

For PCR analysis, analysis can be performed using a single, unambiguously identified fetal cell. For karyotyping, the analysis can be performed using as few as five cells in metaphase. The number of cells necessary to obtain 5 metaphase cells will vary depending on the method used to induce metaphase and the length of culture required. For cells selected to have 2C or greater DNA, a substantially shortened culture period may be used.

Alternatively, ways can be envisaged of identifying monozygosity (indicative of the presence of a monogenic disease) in a mixed cell population containing minimal fetal material including as few as one fetal cell in ten cells.

Following sorting, the separated cells can be washed twice in a physiologic buffer and resuspended in an appropriate medium for any subsequent analysis to be performed on the cells.

Post-Recovery Processing

Following the present recovery method, the fetal cell can be used in the same manner as fetal cells obtained by other methods such as amniocentesis and chorionic villus biopsy. The cells can be used a source of DNA for analysis of the fetal alleles, as by polymerase chain amplification. PCR analysis methods have been used to detect, for example, fetal sex, β-thalassemia, phenylketonuria (PKU), Duchenne's muscular dystrophy.

Alternatively, the cells can be cultured in the same manner as biopsy materials for karyotyping analyses. However, the incubation period may be significantly shortened if a DNA content of greater than or equal to 2C is used as a selection criterion.

This invention is further illustrated by the following specific but non-limiting examples. Temperatures are given in degrees Centigrade and concentrations as weight percent unless otherwise specified. Procedures which are constructively reduced to practice are described in the present tense, and procedures which have been carried out in the laboratory are set forth in the past tense.

EXAMPLE 1

Preparation of Labeled Antibodies

Two monoclonal antibodies specific for two HLA A locus alleles were labeled. The antibody designated GSP 16.1 (Anti-A11, IgM monoclonal antibody from Genetic Systems, Seattle, Wash.) was labeled with FITC. The antibody designated GSP 20.1 (Anti-A2, IgG monoclonal antibody from Genetic Systems, Seattle, Wash.) was labeled with biotin. Cells reacted with the biotinylated antibody were subsequently reacted with PE-labeled strepavidin. The reagents used to purify and label the antibodies are described below.

| Biotinylation Buffer | |
|---|---|
| 0.42 gm $Na_2CO_3$ | |
| 8.06 gm $NaHCO_3$ | |
| QS to 1 liter, pH to 8.4 | |
| FITC Conjugation Buffer | |
| 3.18 gm $Na_2CO_3$ | |
| 5.86 gm $NaHCO_3$ | |
| QS to 1 liter, pH to 9.6 | |
| FITC (Sigma Chemical Co., cat. #F-7250) | |
| Stock Solution FITC: | Dissolve 10 mg in 1 ml DMSO (dimethylsulfoxide) |
| Working Solution FITC: | Dilute stock to 1 mg/ml in FITC conjugation buffer |
| Biotin (Molecular Probes, cat. #S-1582) | |
| Stock Solution Biotin: | Dissolve 10 mg in 1 ml DMSO |
| Working Solution Biotin: | Dilute stock to 1 mg/ml in DMSO |

For the IgG antibody (GSP 20.1), the antibody was first purified by column chromatography using a MAB-Trap G Kit (Pharmacia LKB) to remove other proteins, particularly albumin. This kit utilizes Protein G Sepharose 4 Fast Flow Chromatography media. (Use of Protein G Sepharose is equivalent.) The antibody-containing eluate (15 ml) was concentrated in an Amicon B125 concentrator until the final volume was approximately 2.0 ml (approximately four times the original volume). The antibody was removed from the concentrator to a 12×75 mm test tube. The volume was adjusted to exactly 2.5 ml with biotinylation buffer.

The IgM antibody was not pre-purified. A 0.5 ml antibody sample diluted to 2.5 ml with FITC conjugation buffer.

A PD-10 column from Pharmacia LKB was washed with 25 ml of the appropriate conjugation buffer (FITC conjugation buffer for the FITC-labeled antibody and biotin conjugation buffer for the biotinylated antibody).

The 2.5 ml sample of each antibody was applied to the appropriate column. When the column stopped dripping, a 3 ml aliquot of the appropriate conjugation buffer was applied. Each antibody-containing eluate was collected.

Each eluate was concentrated in an Amicon B125 concentrator until the final volume was 1 ml. The antibody was removed from the concentrator and placed in a 1.5 ml microcentrifuge tube. The amount of protein present was assessed using a kit (Protein Assay Kit #2, BioRad, Richmond, Calif.) that utilizes the Bradford method of protein quantitation.

Once the quantity of antibody (the amount of protein) was calculated, the FITC and biotin were added as follows. A 100 µl aliquot of the working solution of FITC per mg of protein was added to the IgM antibody. A 120 µl of working solution of biotin/mg protein was added to the IgG antibody. Each solution was mixed, and each tube was covered with aluminum foil and rocked on a hematology blood rocker overnight at room temperature.

One PD-10 column for each antibody was prepared by running 25 ml of Phosphate Buffered Saline (PBS), pH 7.4 (0.01 M phosphate, 0.15 M NaCl) through it. Following the incubation, each antibody preparation was diluted to 2.5 ml with PBS and layered over the column. When the column stopped dripping, a 3 ml aliquot of PBS was run through and the eluate was collected.

Each antibody was again concentrated in the Amicon B125 to a final volume of 1 ml. The protein content was again quantitated, and the final concentration was adjusted to 40 µg/ml. In the case of the IgM antibody, the amount of antibody present was estimated to be one-half of the total protein present and was diluted to 40 µg/ml. Bovine serum albumin (BSA) was added to a final concentration of 10 mg/ml and sodium azide was added to a final concentration of 0.1%.

EXAMPLE 2

Preparation of Cells for Labeling

Heparinized whole blood (30 ml) of each sample was layered onto room-temperature Ficoll-Hypaque (Pharmacia-LKB) gradient material at a ratio of 5 ml blood to 3 ml ficoll in separate tubes. The tubes were spun in a swinging bucket centrifuge for 30 minutes at 400 g. The mononuclear layer of each was removed to another tube and washed twice with RPMI 1640 tissue culture media (Mediatech, Inc., Herndon, Va.) with 5% autologous plasma. The samples were then counted on a hemocytometer, adjusted to $5 \times 10^7$/ml in RPMI, then recounted.

EXAMPLE 3

Labeling Cells in a Blood Sample

Labeled antibody is usually used at a concentration of about 2 µg/$10^6$ cells. In this case, 50 µl of the antibody per $10^6$ cells was used for staining. The cells were stained and sorted effectively using that amount of antibody. The cells ($10^6$ cells in 100 µg of RPMI 1640 tissue culture media plus 5% autologous plasma), prepared as described in Example 2, were stained as described below to assess the conjugation of the label to the antibodies.

Tube #1——No antibody added (negative)
Tube #2——GSP 16.1 (Anti-A11, IgM monoclonal antibody) FITC conjugated; 50 µl
Tube #3——GSP 20.1 (Anti-A2, IgG monoclonal antibody) Biotin conjugated; 50 µl
Tube #4——GSP 16.1 + GSP 20.1; 50 µl of each The tubes were mixed and incubated in the dark at 4° C. for 30 minutes. After this time, 10 µl of TAGO (Burlingame, Calif.) PE-strepavidin was added to tubes #3 and #4. This reagent reacts with biotin lending to a biotin/avidin-PE complex which allows the biotin-labeled cells to be fluorescent. The cells were incubated an additional 30 minutes after which the cells were washed twice with ice cold PBS and resuspended in 1 ml of PBS.

EXAMPLE 4

Sorting Labeled Cells

Cells which were labeled as described in Example 3 were subjected to flow cytometric analysis using log green fluorescence (FITC) versus log red fluorescence (PE). (The cells were from a donor [donor A] having the HLA type A2, A11.) This results in a plot that is termed a two-dimensional (2D) plot, contour plot (if contours are drawn), dot plot (if dots are used to represent cells present) or cytogram. When the X-axis representing FITC and the Y-axis representing PE fluorescence are plotted against one another, the resulting graph can be divided into four quadrants. Lower left is where the negative or unstained cells fall. Lower right is where the FITC-labeled (green) cells fall. Upper left is where the PE-labeled (red) cells fall. Upper right is where the FITC- and PE-labeled (green and red) cells fall.

This property of cell identification based upon their labeling characteristics as they fall into the various quadrants of the graph was used to locate and subsequently sort out those located cells.

EXAMPLE 5

Dilution Studies to Evaluate Rare Cell Sorting

In these studies, cells from a blood sample from donor A (sample A) were mixed with cells from a blood sample from donor B (sample B) to mimic rare event cell analysis/sorting using a flow cytometer. This series of experiments was performed to evaluate the ability of flow cytometry to not only define but also isolate these rare cells. These studies were performed by diluting blood from two individuals who have one A locus allele in common. In this way, a predetermined number of cells from each individual were known to be present in a sample.

Antigens for GSP 16.1 and GSP 20.1 are both found on the surface of sample A cells. These cells, when reacted with these monoclonal antibodies, had both red and green fluorescence on their surface. Antigen GSP 20.1 is also found on the surface of sample B cells. These cells, when reacted with this monoclonal antibody, had only red fluorescence on their surface. Thus, the labeling patterns mimic the patterns of a pregnant woman and the fetus.

Sample A was mixed into sample B at ratios of 5%, 1%, 0.1% and 0.001%. In the second study, sample A was mixed into sample B at ratios of 1%, 0.1%, 0.001% and 0.0001%. The dilutions of A into B were calculated so that at least 1000 cells of A were present in the test tube.

The cells were labeled according the procedure in Example 3. Monoclonal antibodies GSP 16.1 and GSP 20.1 were both added to each of the tubes of mixed cells using 50 μl of antibody prepared as described in Example 1 per 10$^6$ cells. The cells were vortexed, and the tube was covered with aluminum foil and placed on an ice pack which was mounted on a hematology blood rocking device.

After the antibody incubation, strepavidin-phycoerythrin (TAGO) was added to each tube of biotin-labeled cells using 10 μl of undiluted PE-strepavidin per 10$^6$ cells. The cells were again vortexed and incubated as previously for another 30 minutes.

Following the incubation, the samples were centrifuged at 1000 g for 3 minutes, washed twice with ice cold PBS, resuspended in RPMI to approximately the original volume and placed on ice.

A separate set of three control tubes containing 10$^6$ sample A cells only was reacted in the same manner as above with GSP 16.1, with GSP 20.1 and with GSP 16.1 in combination with GSP 20.1. A fourth aliquot of cells was left untreated with monoclonal antibodies. This group of four tubes was used to assess the antibody labeling of the cells in the study, and to set the flow cytometry instrument for color compensation, log amplification offset, signal gains, etc. The fluorescence parameters of the instrument were adjusted to produce four quadrant separation of the cells (as discussed previously).

The lowest dilution tubes were analyzed/sorted first. Because the cells in this study were fresh, treated with mild centrifugation and kept at low temperatures, there was minimal debris and clumping of the cells as evaluated by the 90 degree versus forward light scatter parameter. The cells formed a tight, dense cluster on the display.

Only one region (gate) was defined for sorting. This was an area where the dual-labeled sample- A cells would fall on log green versus log red fluorescence parameter display. By defining only one region, the computer had to make one decision in the evaluation of which cells to sort. If the cell fell into the defined gate region of the display, the cell was sorted.

The instrument was set to sort in one drop deflection/purity mode. This means a cell is sorted only if it can confidently be sorted without an unwanted cell being sorted with it. The inclusion of unwanted cells can occur if the cells are located in close proximity to one another resulting in unwanted cells being included in a drop of fluid including wanted cells. This one drop deflection/purity mode lends an added discrimination to the process resulting in a higher percentage of purity in the sorted cells of choice.

The average speed of the sort was approximately 10,000 cells/second. As the cells passed through the instrument, statistics were computed to evaluate the number of cells falling in the sort gate region as well as the number of cells which the instrument sorted.

A collection apparatus for the sorted cells consisted of a 10 ml beaker fitted into a solid support located directly under the sort streams. These beakers are layered with 100 to 200 μl of approximately 50% autologous plasma in RPMI. This layer helps to cushion the cells when they enter the collection vessel.

After at least 3,000 of the cells which were located in the gated region were sorted, the contents of the beaker was poured into another test tube and resubmitted to the flow cytometer for statistical analysis. This process of evaluating the efficacy of the sorting procedure by analyzing the sorted cells using the instrument is referred to as "playback", "sort playback", or simply, "second pass". The statistics obtained from this evaluation of the sorted cells provides information on the alteration in the percentage of the two cell populations from the original tube due to the sort process. It is from this analysis of the sorted cells that the percentage of purity or enrichment of the sorted population can be evaluated.

Using this process, the study demonstrated that in tubes where sample A was diluted at or greater than 0.01%, the flow cytometer was not able to discriminate the signal of the dual-labeled cells as clearly as with the lower dilution. The cells were discriminated. However, the reliability of detecting only the rare cells starts to diminish. This is attributed to statistical problems related to the instrument whereby stray signals caused by inherent noise in the system due to cell clumps, debris, etc., may be evaluated in the region designated for our rare cells. To overcome this limitation, additional parameters, such as a third fluorescent color, cell size, etc. can be used to locate the rare cells.

The study also demonstrated that in tubes where A was diluted at 0.01% and greater, the number of cells which were sorted were less than 3,000. On the playback, the reliability of the analysis was hindered because there were so few cells amidst a pool of noise. This was best seen when an analysis of a playback of a 0.01% dilution tube showed an enrichment of this population to 30%. The next higher dilution tube (0.001%) was sorted directly onto a microscope slide coated with autologous plasma (dry).

Evaluation of the wet mount of this sorted population using a fluorescence microscope revealed nearly 60% of the cells present carried the dual label. Visual inspection revealed a background of dye crystals, debris, etc. which, if played back, would have been picked up by the flow cytometer and counted resulting in what would appear as a lower overall recovery of dual-labeled cells. Less diluted samples are expected to have higher purity than more diluted samples. Therefore, the 0.01% dilution would be expected to have greater than 60% purity.

The evaluation of the dilution-sort studies demonstrated that the present method makes it possible to locate, sort and enrich the diluted cell population appreciably from its original low percentage. In summary, the percentage of sample A cells that were sorted and the percentage of sorted cells, as determined by evaluating the population by FACS is listed below. The evaluation by visual inspection on a slide, as described above, is also shown for a 0.001% dilution.

| (pre-sort) | (post-sort) |
| --- | --- |
| 5% | 75% |
| 1% | 60% |
| 0.1% | 55% |
| 0.01% | 30% |
| 0.001% | 60% (determined visually) |

The limits of discrimination of the number of cells in a gated region using two fluorescence parameters as determined in this study was about 0.01%. Cells falling in this region at higher dilution levels appear to be overestimated.

EXAMPLE 6

Repeat of Dilution Studies

The study described in Example 5 was repeated, including repetition of the monoclonal antibody labeling process. The limits of discrimination in the second study again were at the 0.01% level. The cells from these studies were sorted onto slides coated with plasma and air dried. Approximately 100 cells from dilutions ranging from 1% through 0.0001% were sorted.

EXAMPLE 7

Dilution Studies Using Single-Labeled Rare Cells

Another study was performed as described in Example 6 in which the single-labeled cells were diluted to be the rare cells. (The antibody labeling procedure was not repeated.) Sample A was treated as the maternal, dual-labeled cells and sample B as the fetal, single-labeled cells at dilutions of 0.1, 0.01 and 0.001%. The results obtained were similar to those described in Example 5, above. This demonstrates that the fetal cells can be separated from the maternal cells based upon a single fluorescent label. This more closely mimics the inventive method since the mother antigens can be determined, allowing her cells to be dually labeled. As demonstrated by this study, any combination of the four quadrants where cells can be placed (unstained, red only, green only and red plus green) can be used to separate/sort the cells of interest.

As shown in Examples 5 through 7, a distinction was made between sample A cells and sample B cells based upon fluorescence characteristics following labeling with antibodies for HLA antigens where the labeled cells shared a single antigen of one HLA locus.

What is claimed is:

1. A method for recovering fetal cells from a blood sample of a pregnant woman having different first and second antigens expressed by a first and a second HLA allele, said method comprising:
   a. combining the cells of said sample with a first antibody specific for said first antigen and labeled with a first florochrome and with a second antibody specific for said second antigen labeled with a second, different fluorochrome for a period of time sufficient for antibody binding to produce a sample containing labeled cells;
   b. separating double-labeled cells of said sample from single-labeled and unlabeled cells using fluorescence-activated cell sorting to produce separated, single-labeled and unlabeled cells; and
   c. recovering said separated, single-labeled and unlabeled cells.

2. The method of claim 1 wherein said blood sample is purified to remove red blood cells prior to combination with said antibodies.

3. The method of claim 2 wherein said purification is performed using a gradient material having a density intermediate between red blood cells and lymphocytes.

4. The method of claim 2 wherein said purification is performed using a hypotonic solution.

5. The method of claim 1 wherein said first and said second HLA alleles are from different HLA loci.

6. A method for recovering fetal cells from a blood sample of a pregnant woman having different first and second antigens expressed by a first and a second allele of an HLA locus, method comprising:
   a. combining the cells of said sample with a first antibody specific for said first antigen and labeled with a first fluorochrome and with a second antibody specific for said second antigen and labeled with a second, different fluorochrome for a period of time sufficient for antibody binding to produce a sample containing labeled cells;
   b. separating double-labeled cells of said sample from single-labeled cells using fluorescenceactivated cell sorting to product separated, single-labeled cells; and
   c. recovering said separated, single-labeled cells.

7. The method of claim 6 additionally comprising the step of determining the alleles of said pregnant woman for at least two HLA loci.

8. The method of claim 7 wherein said HLA loci are selected from the group consisting of A, B, and C.

9. The method of claim 7 wherein said HLA loci are selected from the group consisting of DR, DQ, and DP.

10. The method of claim 7 comprising the additional step of obtaining DNA from said recovered fetal cells.

11. The method of claim 7 comprising the additional step of culturing said recovered fetal cells.

12. A method for obtaining fetal cells from the blood of a pregnant woman comprising:
   a. determining the antigens for at least one HLA locus wherein said pregnant woman has two different antigens;
   b. combining the cells of said sample with a first antibody specific for one antigen of said HLA locus and labeled with a first fluorochrome and with a second antibody specific for the other antigen of said HLA locus labeled with a second, different fluorochrome for a period of time sufficient for antibody binding to produce a sample containing labeled cells;
   c. separating cells having two different fluorescent labels from cells having a single fluorescent label using fluorescence-activated cell sorting to separate single-labeled cells; and
   d. recovering said single-labeled cells.

13. The method of claim 12 wherein the antigens of said HLA locus are determined using serological methods.

14. The method of claim 12 wherein the antigens of said HLA locus are determined by using DNA analysis methods.

15. The method of claim 12 wherein said fluorescent labels are fluorescein and phycoerythrin.

16. A method for recovering fetal cells for karyotyping from a blood sample of a pregnant woman having different first and second antigens for an HLA locus, said method comprising:
   a. combining the cells of said sample with a first antibody specific for said first antigen and labeled with a first fluorochrome and with a second antibody specific for said second antigen labeled with a second, different fluorochrome for a period of time sufficient for antibody binding to produce a sample containing labeled cells;
   b. separating cells having two different fluorescent labels from cells having a single fluorescent label using fluorescence-activated cell sorting to separate single-labeled cells;
   c. recovering said single-labeled cells; and
   d. culturing said recovered fetal cells under suitable conditions for a period of time sufficient to produce metaphase cells.

17. The method of claim 16 additionally comprising selectively removing recovered fetal cells which have a DNA content which is greater than 2C using fluorescence-activated cell sorting.

* * * * *

UNITED STATES PATENT AND TRADEMARK OFFICE
CERTIFICATE OF CORRECTION

PATENT NO. : 5,153,117
DATED : October 6, 1992
INVENTOR(S) : Malcolm J. Simons It is certified that error appears in the above-identified patent and that said Letters Patent is hereby corrected as shown below:

```
Title page, item [57]
Abstract, line 8:  delete "material" and insert -
--maternal--

Column 7, lines 33-34: delete "Ora pp-106 Pharmacia)" and
insert --or a PD-10 (Pharmacia)--

Column 15, line 41: delete "florochrome" and insert
--fluorochrome--.

Column 16, line 5: delete "fluorescenceactivated" and
insert --fluorescence-activated--
```

Signed and Sealed this

Thirtieth Day of November, 1993

Attest:

BRUCE LEHMAN

*Attesting Officer*      *Commissioner of Patents and Trademarks*